United States Patent [19]

Stoller

[11] 4,384,002

[45] May 17, 1983

[54] ODORLESS, NON-VOLATILE FORMALDEHYDE FOR USE AS A PESTICIDE

[76] Inventor: Benjamin B. Stoller, c/o Stoller Research Co., P.O. Box 1339, Santa Cruz, Calif. 95061

[21] Appl. No.: 261,904

[22] Filed: May 8, 1981

[51] Int. Cl.³ .................. A01N 35/02; A01N 37/00
[52] U.S. Cl. ................................ 424/315; 424/334
[58] Field of Search ............................. 424/315, 334

[56] References Cited

U.S. PATENT DOCUMENTS

| | | | |
|---|---|---|---|
| 969,661 | 9/1910 | Schneider | 424/334 |
| 2,110,943 | 3/1938 | Remensnyder | 424/334 |
| 3,942,969 | 3/1976 | Carroll, Jr. et al. | 71/5 |
| 4,079,543 | 3/1978 | Stoller | 47/1.1 |
| 4,170,842 | 10/1979 | Stoller | 47/1.1 |

OTHER PUBLICATIONS

Yasumasu, Chemical Abstracts, vol. 79:124909d, (1973).

*Primary Examiner*—Allen J. Robinson
*Attorney, Agent, or Firm*—Robert G. Slick

[57] ABSTRACT

Formaldehyde sodium bisulfite is employed as a fungicide, pesticide and disinfectant. It is particularly useful in mushroom growing houses.

2 Claims, No Drawings

ODORLESS, NON-VOLATILE FORMALDEHYDE FOR USE AS A PESTICIDE

SUMMARY OF THE INVENTION

Formaldehyde has been used as a fungicide, pesticide and disinfectant for many years. However, both formaldehyde gas and the vapor of its aqueous solution have a pungent odor. Its volatile vapors are intensely irritating to the mucous membranes of the nose and throat. Furthermore, it is so irritating to the eyes that it causes lacrimation or tears.

If formaldehyde can be made odorless and non-volatile, and still maintain its fungicidal and pesticidal properties, its usefulness would be greatly extended. Formaldehyde could then be used in enclosed places such as mushroom growing houses and in greenhouses.

The present usage of formaldehyde is limited to spraying or dipping in outside areas where there is plenty of ventilation. When formaldehyde is used for fumigation in an enclosed area, no one can enter the premises until after aeration. When formaldehyde is used to "sterilize" soil or peat as used in greenhouse practices, and in mushroom growing for preparation of "potting soil" or the "casing layer" (in mushroom growing), the liquid formaldehyde is poured on a heap of soil or peat or both, or the liquid is pumped into the pile, then covered over with plastic sheeting and let stand for a few days. After this kind of "sterilizing," there is considerable work in freeing the soil or peat of the residual volatile formaldehyde so that these materials may be used in growing plants or mushrooms.

My invention pertains to the use of odorless, non-volatile formaldehyde, which has no odor, no volatile vapors and causes no lacrimation or mucous membrane irritation. The odorless formaldehyde of the present invention may be used in enclosed buildings. Furthermore, this odorless formaldehyde, unlike ordinary formaldehyde, is not toxic to plants, in particular, the mushroom mycelium as in mushroom growing, when used in proper concentrations. So it is not necessary to "sterilize" with ordinary formaldehyde as previously described, rather, the odorless formaldehyde is merely added to the soil or peat so that these materials are immediately ready for use. Another very important advantage is that in the former method of "sterilizing," the protective effect of the formaldehyde was used up, and was thus lost when the soil or peat was aerated. On the other hand, the formaldehyde of this odorless formaldehyde chemical compound is only slowly released (as later explained) so that protection continues during growth of plants or mushrooms.

Formaldehyde is made odorless and non-volatile by combining ordinary formaldehyde with sodium bisulfite. The chemical compound formed by this combination is known as sodium formaldehyde bisulfite; formaldehyde sodium bisulfite, hydroxymethane sulfonic acid, sodium salt; and methylolsulfonic acid sodium salt. Formaldehyde sodium bisulfite is the preferred name and is used hereafter.

SUMMARY OF THE PRIOR ART

Formaldehyde with sodium bisulfite is used to make these compounds. These chemical compounds of sodium formaldehyde bisulfite, etc. are well known and methods for some of its preparations have even been patented. The claims made herein pertain only to its usage as a fungicide and pesticide.

An examination of a definitive "Dictionary of Pesticides," namely "Nanogen Index" by Kingsley Packer, and published by Nanogen International, P.O. Box 487, Freedom, California, 95019, revealed no mention of these chemical compounds, namely, sodium formaldehyde bisulfite, etc. used as fungicides or pesticides. Furthermore, the additions to this Index for 1976, 1978 and 1979 also make no reference to the chemical compound which is the subject of this patent application. Only regular formaldehyde is mentioned in this index as a pesticide.

DESCRIPTION OF THE PREFERRED EMBODIMENTS

I have discovered that this formaldehyde sodium bisulfite may be sprayed or mixed with soil or peat for casing mushroom beds, or eradicating diseases with beneficial results to the mushroom crop. This chemical is not toxic to the mushroom mycelium that grows through compost, provided proper concentrations are employed. This chemical may be used in both liquid and solid-granular forms.

How this formaldehyde sodium bisulfite functions as a fungicide and pesticide is believed to be as follows: The sodium bisulfite part of this combination is slowly oxidized by the oxygen of the air (and possibly by the quinones secreted by the mushroom mycelium) to sodium sulfate. Since sodium sulfate has no affinity for formaldehyde, the latter escapes as a volatile gas. In this manner small amounts of formaldehyde are released to provide the needed toxicity to pests. Fortunately, the gradual release of formaldehyde from this combination is more toxic to pests and disease producing organisms than to hosts (mushroom mycelium, for example). So that the disease producer is destroyed allowing a healthy growth of plants.

Formaldehyde sodium bisulfite is a true chemical compound, not a mixture of two chemicals. For example, when formaldehyde is mixed with a proteinaceous material as described in U.S. Pat. No. 3,942,969, Mar. 9, 1976, volatile formaldehyde may be detected from this mixture; whereas no volatile formaldehyde is detected from the chemical compound formaldehyde sodium bisulfite. This chemical compound produces a slow release of formaldehyde only by the oxidation of the "sulfite" to the "sulfate."

For mixing with peat, to be used to "case" spawned compost in mushroom beds, 4,4 grams of the solid powder, formaldehyde sodium bisulfite are mixed with 70 lbs. peat, which is sufficient peat to case 22 square feet of bed space. It has been found that quantities of from 1 to 10 grams per 70 pounds of casing material are effective. At present, Benlate and Zineb fungicides are mixed with the peat casing to prevent diseases, especially Mycogone and Verticillium, known to mushroom growers as "Bubbles." The advantage of using formaldehyde sodium bisulfite in place of these two fungicides is that resistance of these diseases to formaldehyde is unknown and is probably impossible due to the chemical configuration of formaldehyde. Resistance is building up now against Benlate and Zineb, so that mushroom growers are forced to search for new fungicides. In our tests with formaldehyde sodium bisulfite under conditions of mixing with peat casing as described, the occurences of these diseases was reduced to 0.1%.

Another advantage of formaldehyde sodium bisulfite over Benolate and Zineb is that the former costs only half as much.

Formaldehyde sodium bisulfite may also be sprayed on mushroom beds where mushrooms have been growing. After picking off about half of the mushroom crop from the mushroom beds (that is after the "second break") frequently, there are signs of Verticillium and Mycogone diseases, that is, a small percentage of deformed mushrooms. To prevent a greater break-out or spread in the ensuing "third break" the mushroom grower picks the beds clean of mushrooms and sprays the beds with fungicides like Benlate and Zineb. As a rule, after spraying with these fungicides the diseased mushrooms will appear about as numerous as controls (sprayed with water only). So these fungicides are not satisfactory once "Bubbles" appears on beds.

When mushroom beds are cleaned of mushrooms as described above, before the "third break," and sprayed with formaldehyde sodium bisulfite at the rate of 20 ounces to 25 ounces of the liquid form to 100 gallons of water, (about 300 gallons for 6500 square feet) mushroom growing in the "third break" are almost free of the "Bubbles" deformities, and an abundant crop is harvested. Such an aqueous solution has a strength of about 0.002% by weight. Concentrations of from 0.001 to 0.1% are suitable for use. Whereas on the control beds which were sprayed only with water, an increased break-out of "Bubbles" occurs, and the mushroom crop is scanty. This decided advantage is obtained by spraying with formaldehyde sodium bisulfite. Previously, such beds could not be sprayed with formaldehyde, because the odor and volatile fumes of ordinary formaldehyde made such spraying in enclosed areas unendurable for the workers.

Accordingly, the advantages of my new method and process are as follows:

1. Making formaldehyde odorless and non-volatile, permits use of formaldehyde in enclosed places, such as mushroom houses and greenhouses.

2. Formaldehyde sodium bisulfite prevents or drastically reduces diseases such as "Bubbles" from occurring when this chemical is mixed with soil or peat casing as in the practice in mushroom growing, and also for potting soil in greenhouse practices.

3. Formaldehyde sodium bisulfite sprayed on mushroom beds which have already shown symptoms of diseases such as "Bubbles" will prevent spread of this disease and allow good crops to continue to grow.

4. Formaldehyde sodium bisulfite is a type of fungicide and pesticide that shows no resistance to fungus diseases such as "Bubbles."

5. Formaldehyde sodium bisulfite costs about one half as much as other fungicides.

6. Unlike ordinary formaldehyde, which must be expelled before the soil or peat can be used, formaldehyde sodium bisulfite remains in the soil or peat and the formaldehyde is slowly released by the oxidation of the sulfite. Accordingly, protection from disease is extended for some time, allowing the crop to be harvested.

Subject matter to be claimed is:

1. The method of inhibiting the growth of insects, fungi or bacteria in a casing for mushrooms or in mushroom beds comprising spraying an aqueous solution of formaldehyde sodium bisulfite onto the mushroom bed wherein about 20 to 25 ounces of liquid formaldehyde sodium bisulfite are mixed with 100 gallons of water and applied to about 2200 square feet of bed.

2. The method of claim 1 wherein the concentration of formaldehyde sodium bisulfite is from about 0.001 to 0.1% by weight.

* * * * *